(12) United States Patent
Middaugh et al.

(10) Patent No.: US 10,583,229 B2
(45) Date of Patent: Mar. 10, 2020

(54) NEGATIVE PRESSURE DEVICE AND METHOD (71) Applicant: Aatry Medical, LLC, Cleveland, OH (US)

(72) Inventors: Richard L. Middaugh, Rocky River, OH (US); Timothy Wojciechowski, Westlake, OH (US); Thomas E. Lash, Chardon, OH (US); Sundar Manickam, Avon Lake, OH (US); John D. Wolter, Berea, OH (US); John Buan, Maple Grove, MN (US)

(73) Assignee: Aatru Medical, LLC, Cleveland, OH (US)

(*) Notice: Subject to any disclaimer, the term of this patent is extended or adjusted under 35 U.S.C. 154(b) by 0 days.

(21) Appl. No.: 16/199,839

(22) Filed: Nov. 26, 2018

(65) Prior Publication Data
US 2019/0091382 A1 Mar. 28, 2019

Related U.S. Application Data (63) Continuation of application No. PCT/US2018/025980, filed on Apr. 4, 2018, which is
(Continued)

(51) Int. Cl.
A61M 1/00 (2006.01)
A61F 13/00 (2006.01)
(Continued)

(52) U.S. Cl.
CPC ....... *A61M 1/009* (2014.02); *A61F 13/00068* (2013.01); *A61F 13/0206* (2013.01);
(Continued)

(58) Field of Classification Search
CPC .. A61M 1/009; A61M 1/0092; A61M 1/0066; A61M 1/0052; A61M 1/0084;
(Continued)

(56) References Cited

U.S. PATENT DOCUMENTS

4,875,473 A 10/1989 Alvarez
5,060,642 A 10/1991 Gilman
(Continued)

*Primary Examiner* — Adam Marcetich
*Assistant Examiner* — Jessica R Arble
(74) *Attorney, Agent, or Firm* — Rankin, Hill & Clark LLP (57) ABSTRACT A negative pressure device includes a drape, a wicking element, a sealing element, a reactor, a chamber and an air permeable liquid impervious element. The drape includes an opening and is made from a flexible material that inhibits passage of liquid and air through the drape other than through the opening. The wicking element is covered by the drape. The sealing element surrounds the wicking element and cooperates with the drape to define an enclosed volume covered by the drape and surrounded by the sealing element. The reactor is configured to react with a gas found in air to consume the gas. The chamber is in fluid communication with the reactor and the enclosed volume via the opening. The chamber is configured to maintain a predefined chamber volume while the gas is being consumed from the enclosed volume.

15 Claims, 9 Drawing Sheets

Related U.S. Application Data a continuation-in-part of application No. 15/478,327, filed on Apr. 4, 2017, now Pat. No. 10,046,095.

(51) Int. Cl.
*A61F 13/02* (2006.01)
*A61F 13/537* (2006.01)

(52) U.S. Cl.
CPC ...... *A61F 13/0213* (2013.01); *A61F 13/0216* (2013.01); *A61M 1/0066* (2013.01); *A61M 1/0092* (2014.02); *A61F 13/537* (2013.01); *A61M 1/0052* (2014.02); *A61M 1/0084* (2013.01); *A61M 2205/3331* (2013.01)

(58) Field of Classification Search
CPC ............. A61M 2205/3331; B01J 19/00; A61F 13/537; A61F 13/00068; A61F 13/0206; A61F 13/0213; A61F 13/0216
See application file for complete search history.

(56) References Cited

U.S. PATENT DOCUMENTS

| | | | |
|---|---|---|---|
| 5,533,962 A | 7/1996 | Peterman et al. | |
| 5,579,765 A * | 12/1996 | Cox | A61B 5/02042 600/307 |
| 7,361,184 B2 * | 4/2008 | Joshi | A61M 1/0066 602/42 |
| 7,507,870 B2 | 3/2009 | Nielson et al. | |
| 7,779,625 B2 * | 8/2010 | Joshi | A61M 1/0031 60/313 |
| 8,372,049 B2 | 2/2013 | Jaeb et al. | |
| 8,425,478 B2 | 4/2013 | Olson | |
| 8,439,894 B1 | 5/2013 | Miller | |
| 8,604,265 B2 | 12/2013 | Locke et al. | |
| 8,764,732 B2 | 7/2014 | Hartwell | |
| 8,795,247 B2 | 8/2014 | Bennett et al. | |
| 8,808,274 B2 | 8/2014 | Hartwell | |
| 9,061,095 B2 | 6/2015 | Adie et al. | |
| 9,168,330 B2 | 10/2015 | Joshi et al. | |
| 9,283,118 B2 | 3/2016 | Locke et al. | |
| 2005/0070835 A1 | 3/2005 | Joshi | |
| 2009/0299251 A1 | 12/2009 | Buan | |
| 2010/0137775 A1 | 6/2010 | Hu et al. | |
| 2013/0150814 A1 | 6/2013 | Buan | |
| 2015/0057625 A1 | 2/2015 | Coulthard | |
| 2015/0191845 A1 | 7/2015 | Scherson et al. | |
| 2015/0320605 A1 | 11/2015 | Pigg | |
| 2016/0361205 A1 | 12/2016 | Mumby | |
| 2017/0028113 A1 | 2/2017 | Shuler et al. | |
| 2017/0304510 A1 * | 10/2017 | Askem | A61M 1/0088 |

\* cited by examiner

NEGATIVE PRESSURE DEVICE AND METHOD

BACKGROUND

Negative pressure is a term used to describe a pressure that is below normal atmospheric pressure. Known topical negative pressure devices range from cumbersome wrinkle reducing suction apparatuses to wound therapies that include fluid-permeable wound cavity filling elements, covering dressings, reasonably air-tight means for sealing against the skin, and drainage tubes connecting the wound site and cavity filling element to the vacuum source via a fluid collection canister.

To enable a more prolonged application of topical negative pressure, powered systems, which include a vacuum generation source such as a pump, have been developed and many examples of such systems are used today for skin treatments and restorative purposes like the temporary removal of wrinkles. Many of these systems, however, are not convenient for users. Such known systems can be large, heavy, noisy, uncomfortable, and not simple for users to apply and initiate a controlled pressure condition. Such known systems also rely on an outside power or vacuum source to create topical negative pressure conditions.

Such tissue treatment, surgery, and other advanced technical interventions are becoming more common given the occurrence of both the aging population, as well as increasingly compromised patient populations. This trend looks set to continue. In wound care, for example, healthcare professionals are now more likely to encounter wounds that are difficult to manage with complex healing problems. Attempts have been made to produce more simple mechanical devices able to apply topical and negative pressure to a tissue site. It will be appreciated that such a medical device, due to its relative simplicity of design, would be expected to reduce material costs and assembly costs. For example, attempts have been made to use a hand-pump system for the application of topical negative pressure at a tissue site. However, such a system fails to enable easier application by the user, discreet use, and prolonged convenient application of topical negative pressure, and, in fact, re-evacuation is often necessary. These can be serious deficiencies, particularly as many such systems are ideally useable for prolonged periods, such as overnight.

SUMMARY

In view of the foregoing, a negative pressure device includes a drape, a wicking element, a sealing element, a reactor, a chamber and an air permeable liquid impervious element. The drape includes an opening and is made from a flexible material that inhibits passage of liquid and air through the drape other than through the opening. The wicking element is covered by the drape. The sealing element surrounds the wicking element and when applied to skin cooperates with the drape to define an enclosed volume covered by the drape and surrounded by the sealing element. Air within the enclosed volume is inhibited from exiting the enclosed volume other than through the opening. The reactor is configured to react with a gas found in air to consume the gas. The chamber is in fluid communication with the reactor and the enclosed volume via the opening. The chamber is configured to maintain a predefined chamber volume while the gas is being consumed from the enclosed volume. The air permeable liquid impervious element is interposed between the chamber and the enclosed volume and is configured to preclude liquid from entering the chamber.

A method of treating a tissue site includes affixing a drape to skin surrounding a tissue site and covering a wicking element. The drape includes an opening and is made from a flexible material that inhibits passage of liquid and air through the drape other than through the opening. The method further includes sealing around the tissue site with a sealing element cooperating with the drape to define an enclosed volume covered by the drape and surrounded by the sealing element. The method further includes providing a reactor configured to react with a gas found in air to consume the gas, and connecting a chamber to be in fluid communication the reactor and the enclosed volume. The chamber is configured to maintain a predefined chamber volume while the reactor consumes the gas in the enclosed volume. The method also includes precluding liquid from entering the chamber while the reactor consumes the gas in the enclosed volume.

DETAILED DESCRIPTION

Figure 1:
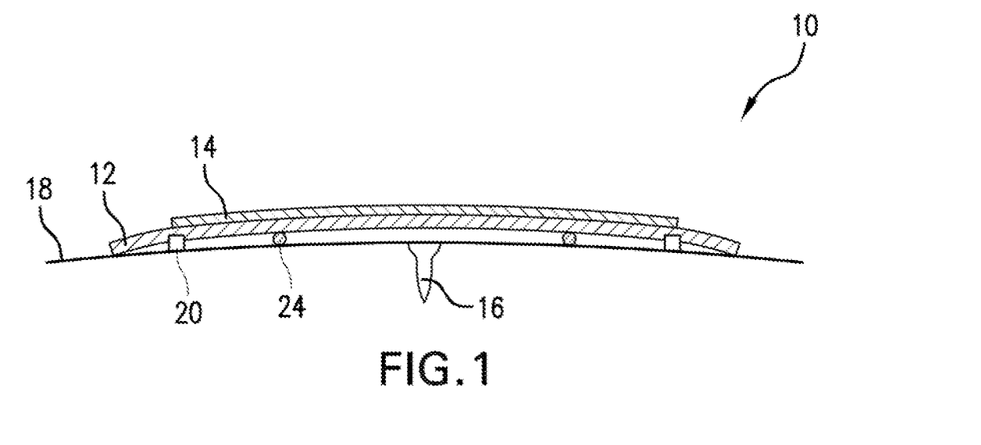
FIG. 1 is a cross-sectional view of a wound covering assembly.

FIG. 1 depicts a wound covering assembly 10 that includes a wound covering membrane 12 and a removable layer 14. The wound covering membrane 12 is configured to allow at least one of liquid and air to pass through the wound covering membrane 12 from a wound site 16 covered by the wound covering membrane 12 to ambient and vice versa. The removable layer 14 covers at least a portion of the wound covering membrane 12. The removable layer 14 is removable from the wound covering membrane 12 when the wound covering membrane 12 is affixed to skin 18 around the wound site 16. The removable layer 14 is configured (e.g., made from a particular material or materials) and connected with the wound covering membrane 12 such that air and liquid are inhibited from passing through the wound covering membrane 12 and the removable layer 14 when the wound covering membrane 12 is affixed to skin 18 surrounding the wound site 16 and the removable layer 14 is connected with the wound covering membrane 12. As such, with the removable layer 14 connected with and covering at least a portion of the wound covering membrane 12, the wound covering assembly 10 is not a "breathable" bandage, and can be referred to as an occlusive bandage.

In the illustrated embodiment, the wound covering membrane 12 is made from a flexible material and can be made from a thin, flexible elastomeric film. Examples of such materials include polyurethane or polyethylene films. Adhesive (not shown) is applied to a skin contacting surface of the wound covering membrane 12 to affix the wound covering membrane 12 to the skin 18. In some instances the wound covering membrane 12 allows only air to pass through, while in other instances the wound covering membrane 12 may allow both air and liquid to pass through. The wound covering membrane 12 may also include openings (not visible in FIG. 1, but another embodiment having at least one opening is described below) and can be configured to inhibit passage of air and liquid through the wound covering membrane 12 other than through the opening(s). For example, the wound covering membrane 12 can made from a material that is air and liquid impermeable, or the wound covering membrane 12 could be coated with a substance, e.g., a hydrogel or a hydrocolloid, or be metallized, to inhibit passage of air and liquid through the wound covering membrane 12 other than through the opening(s). In alternative embodiments, the wound covering membrane 12 can be made from semipermeable materials that can maintain moisture around the wound site 16 while being permeable to water vapor, oxygen, nitrogen and other gases.

Figure 2:
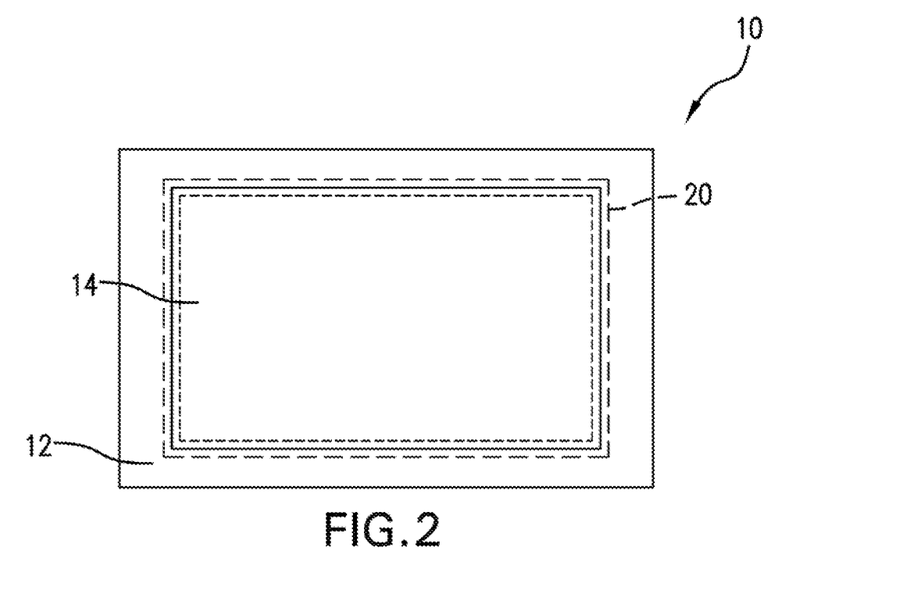
FIG. 2 is a top view of the wound covering assembly depicted in FIG. 1.

The removable layer 14 covers at least a portion of the wound covering membrane 12. Only one removable layer 14 is depicted in FIGS. 1 and 2, however, more than one removable layer 14 can be provided. For example, a plurality of removable layers 14 where each removable layer 14 covers a portion of the wound covering membrane 12. The removable layer 14 can be made from a thin, flexible film. Examples of such materials include polyurethane or polyethylene films. The removable layer 14 is configured to inhibit passage of air and liquid through removable layer 14 when the removable layer 14 is covering and connected with the wound covering membrane 12. The removable layer 14 can made from a material that is air and liquid impermeable, or the removable layer 14 can be coated with a substance, e.g., a hydrogel or a hydrocolloid, or be metallized so as to be air and liquid impermeable.

When the removable layer 14 is removed from the wound covering membrane 12, the wound site 16 is exposed to ambient although through the wound covering membrane 12. When the wound covering membrane 12 is air and liquid pervious, removal of the removable layer 14 can transform the wound covering assembly 10 from an occlusive dressing to a non-occlusive dressing. With the removable layer 14 removed from the wound covering membrane, a pump assembly (examples described below) can be affixed to the wound covering assembly 10 or to the skin 18 to provide negative pressure to the wound site 16, which will be described in more detail below.

The wound covering assembly 10 can also include a sealing element 20 positioned between the skin 18 and the wound covering membrane 12. The sealing element 20 is configured to preclude gas and liquid from passing between the skin 18 and the wound covering membrane 12 when the wound covering membrane 12 is affixed to the skin 18, and is typically in addition to the adhesive used to affix the wound covering membrane 12 to the skin 18. The sealing element 20 operates similar to a gasket and can be made from a hydrogel material, or any other material that can prevent the migration of air and liquid from the wound site 16 under the wound covering membrane 12 and over the skin 18.

With reference to FIG. 2, the removable layer 14 can cover at least the portion of the wound covering membrane 12 bounded by (within) the sealing element 20. When the wound covering membrane 12 is air or liquid permeable, removal of the removable layer 14 can transform the wound covering assembly 10 from an occlusive dressing to a non-occlusive, or "breathable," dressing.

The wound covering assembly 10 can also include at least one spacer element 24 covered by the wound covering membrane 12. The spacer element 24 is configured to maintain spacing between the wound covering membrane 12 and the wound site 16 covered by the wound covering membrane 12 when reduced pressure is applied underneath the wound covering membrane 12 around the wound site 16. The wound covering membrane 12 can be made from a thin film, which allows the wound covering membrane 12 to conform to curves found on the human body but it also tends to be drawn toward the wound site 16 when negative pressure is applied to the wound site 16 underneath the wound covering membrane 12. The spacer element(s) 24 are configured to conform to these curves while maintaining adequate spacing between the wound covering membrane 12 and the wound site 16. Examples of such spacer elements will be described in more detail below with reference to alternative embodiments.

Figure 3:
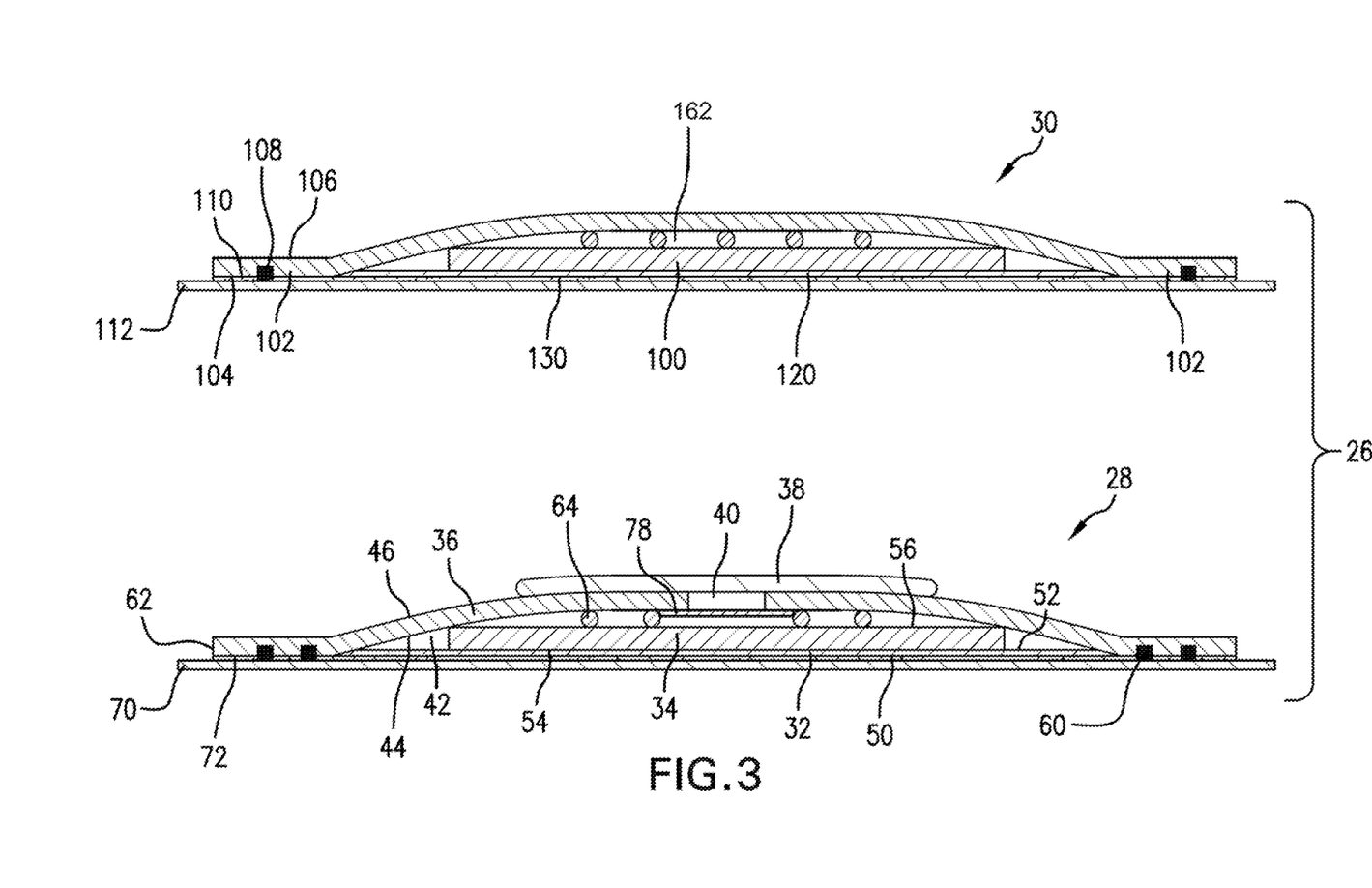
FIG. 3 is a cross-sectional view of a negative pressure device including an alternative wound or tissue covering assembly and a pump assembly prior to affixing the pump assembly to the alternative covering assembly.
Figure 4:
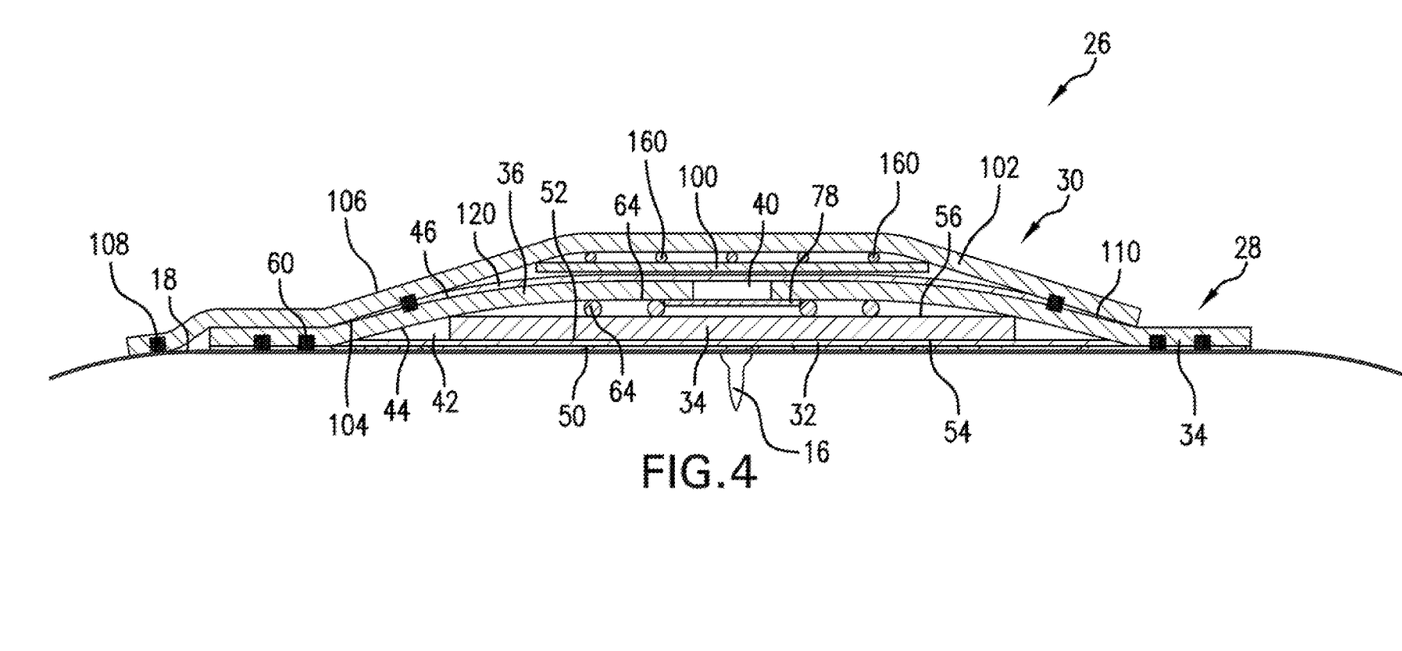
FIG. 4 is a cross-sectional view of the negative pressure device with the pump assembly affixed to the alternative covering assembly.

Referring now to FIG. 3, an illustrative embodiment of a negative pressure device 26 includes an alternative wound covering assembly 28 and a pump assembly 30. The wound covering assembly 28 depicted in FIGS. 3 and 4 is similar in function to the wound covering assembly 10 described above. With reference to FIG. 4, the wound covering assembly 28 is affixed to skin 18 surrounding a wound site 16 to cover the wound site 16. The pump assembly 30 can then be affixed to the wound covering assembly 28 or to the skin 18 around the wound site 16 to provide reduced pressure (typically below that of atmospheric pressure) to the wound site 16. The wound covering assembly 28 can also be used to cover the wound site 16 without the use of the pump assembly 30. Depending on the materials chosen to manufacture the wound covering assembly 28, the wound covering assembly 28 can provide an occlusive dressing or a non-occlusive dressing for the wound site.

With reference back to FIG. 3, the wound covering assembly 28 generally includes a wound contacting element, which can include a wound contact layer 32 or a wicking element 34, a drape 36, which can be similar in function to the wound covering membrane 12 described above, and a peel away layer 38, which can be similar to the removable layer 14 described above. Accordingly, the wound covering membrane 12 and the drape 36 can be used interchangeably, and the removable layer 14 and the peel away layer 38 can also be used interchangeably.

The drape 36 covers the wound contacting element, which can be made up of the wound contact layer 32 and the wicking element 34. The drape 36 includes at least one opening 40 that extends from a lower (inner) surface 44 of the drape 36 to an outer surface 46 of the drape 36. The peel away layer 38 covers the opening 40. The peel away layer 38 is releasable from the drape 36 when the drape 36 is in contact with the skin 18 covering the wound site 16. The peel away layer 38 is connected with the drape 36 in a manner such that air and liquid are precluded from passing through the opening 40 in the drape 36 from the wound site 16 to ambient, and vice versa, when the drape 36 is affixed to the skin 18 surrounding the wound site 16 and the peel away layer 38 is connected with the drape 36 covering the opening 40. As such, the drape 36 and the peel away layer 38 can define an enclosed volume 42 beneath the drape 36 and the peel away layer 38 around the wound site 16 when the drape 36 is affixed to the skin 18 surrounding the wound site 16 and the peel away layer 38 is connected with the drape 36 covering the opening 40.

The wound contacting element can include the wound contact layer 32 or the wicking element 34. As used herein, the word "or" is not mutually exclusive. The wound contact layer 32 can be made from an elastomeric material, such as a polymeric material that has rubber-like properties. The wound contact layer 32 can be made from an elastomeric material that is a thin, flexible elastomeric film. Examples of such materials include a silver coated nylon, a perforated silicone mesh or other materials that will not stick to human tissue. The wound contact layer 32 can include a plurality of openings (not shown) when used in conjunction with the wicking element 34 to allow exudate from the wound site 16 to pass through the wound contact layer 32 and be retained within the wicking element 34. The wound contact layer 32 includes a skin contacting side 50, which contacts the skin 18 or the wound site 16 when the wound covering assembly 28 is placed over the wound site 16 (see FIG. 2). The wound contact layer 32 also includes an upper side 52 opposite the skin contacting side 50 that faces away from the wound site 16 when the wound covering assembly 28 is affixed to the skin 18 over the wound site 16.

The wicking element 34 can be made from an absorbent material capable of absorbing liquid so as to absorb exudate from the wound site 16. The wicking element 34 includes a skin facing side 54 that faces the skin 18 and the wound site 16 when the wound covering assembly 28 is affixed to the skin 18 over the wound site 16. The wicking element 34 can also include an upper side 56 that is opposite the skin facing side 54 and faces away from the skin 18 when the wound covering assembly 28 is affixed to the skin 18 over the wound site 16. The wicking element 34 can be made from a super absorbent polymers and absorbent beads, foams or natural absorbent materials. The wound covering assembly 28 can also be assembled in a manner, which is described in more detail below, to allow for replacement of the wicking element 34 without removal of the wound contact layer 32.

The drape 36 covers the wicking element 34 and the wound contact layer 32. The drape 36 can be similar in function to the wound covering membrane 12 described above, and like the wound covering membrane 12 can also be made from a flexible material and can be made from a thin, flexible elastomeric film. Examples of such materials include polyurethane or polyethylene films. The drape 36 can be configured to inhibit passage of air and liquid through the drape 36 other than through the opening 40. For example, the drape 36 can be made from a material that is air and liquid impermeable, or the drape 36 could be coated with a substance, e.g., a hydrogel or a hydrocolloid, or be metallized, to inhibit passage of air and liquid through the drape 36 other than through the opening 40. In alternative embodiments, the drape 36 can be made from semipermeable materials that can maintain moisture around the wound site 16 while being permeable to water vapor, oxygen, nitrogen and other gases.

The wound covering assembly 28 further includes a sealing element 60, which operates similarly to the sealing element 20 described above. Since the drape 36 can be made from a flexible film-like material, small air passageways may be formed between the skin 18 and the drape 36 when the drape 36 is affixed to the skin 18 around the wound site 16. The sealing element 60 is positioned on the skin contacting side 50 of the wound contact layer 32 or on the lower surface 44 of the drape 36. The sealing element 60 is configured to preclude gas and liquid from passing through any air channels formed between the wound contact layer 32 or the drape 36 and the skin 18 and exiting around a peripheral edge 62 of the drape 36. The sealing element 60 is configured to preclude gas and liquid from passing between the human skin 18 and the wound contact layer 32 (or the wicking element 34 if the wound contact layer 32 is not included) or the drape 36 when the drape 36 and the sealing element 60 are applied to the skin 18. The sealing element 60 operates similar to a gasket and can be made from a hydrogel material, or any other material that can prevent the migration of air and liquid from the wound site 16 under the drape 36 or the wound contact layer 32 and over the human skin 18. The sealing element 60 is schematically depicted in FIGS. 3 and 4, and can be made to include multiple rings or deposited in a manner to provide a tortuous path through which air and liquid must pass between the human skin 18 and the wound contact layer 32 (or the wicking element 34 if the wound contact layer 32 is not included) or the drape 36 when the drape 36 and the sealing element 60 are applied to the skin 18.

The wound covering assembly 28 can also include at least one spacer element 64 covered by the drape 36 when the drape 36 is applied to the human skin 18 around the wound site 16. The spacer element 64 is similar to the spacer element 24 described above. The spacer element 64 is configured to maintain spacing between the drape 36 and the wound site 16 covered by the drape 36 when reduced pressure is applied in the enclosed volume 42. Since the drape 36 can be made from a flexible material, as reduced pressure is applied in the enclosed volume 42, the drape 36 may be drawn towards the skin 18 and the wound site 16. In situations where the pump assembly 30 reacts with selected gases in air to remove these selected gases from the enclosed volume 42 to reduce pressure, having the drape 36 collapse toward the wound site 16 can result in the pressure in the enclosed volume 42 increasing toward ambient, which is undesirable for negative pressure wound therapy. The spacer element 64 can be a frame structure or similar structural element to provide volume control so as to maintain an appropriate spacing between the drape 36 and the wound site 16 when reduced pressure is being applied in the enclosed volume 42. The spacer element 64 could also be a flexible coil spring, which may allow for more flexibility of the wound covering assembly 28 over the wound site 16 when the wound covering assembly 28 is affixed to the skin 18. The spacer element 64 is configured to conform to curves found on the human body while maintaining adequate spacing between the drape 36 and the wound site 16.

Other devices could also be used as a spacer element to adequately space the drape 36 from the wound site 16 when reduced pressure is being applied in the enclosed volume 42. Also, the wicking element 34 can be configured to provide appropriate voids for gases found in air so that reduced pressure can be maintained. For example, the wicking element 34 can be made from a relatively more rigid foam as compared to the drape 36 that maintains gas voids while absorbing exudate from the wound. The wicking element 34 could also be made from the superabsorbent polymers described above that expand and form gas voids, for example between adjacent beads, to provide the aforementioned volume control.

The wound covering assembly 28 can also include a wound drape release liner 70, which can be similar to release liners used in known bandages. The wound drape release liner 70 is disposed over the lower surface 44 of the drape 36. The wound drape release liner 70 is removable to expose an adhesive 72 provided on the lower surface 44 of the drape 36. The wound drape release liner 70 is removed from the drape 36 prior to affixing the wound covering assembly 28 to the skin 18 and over the wound site 16.

Figure 5:
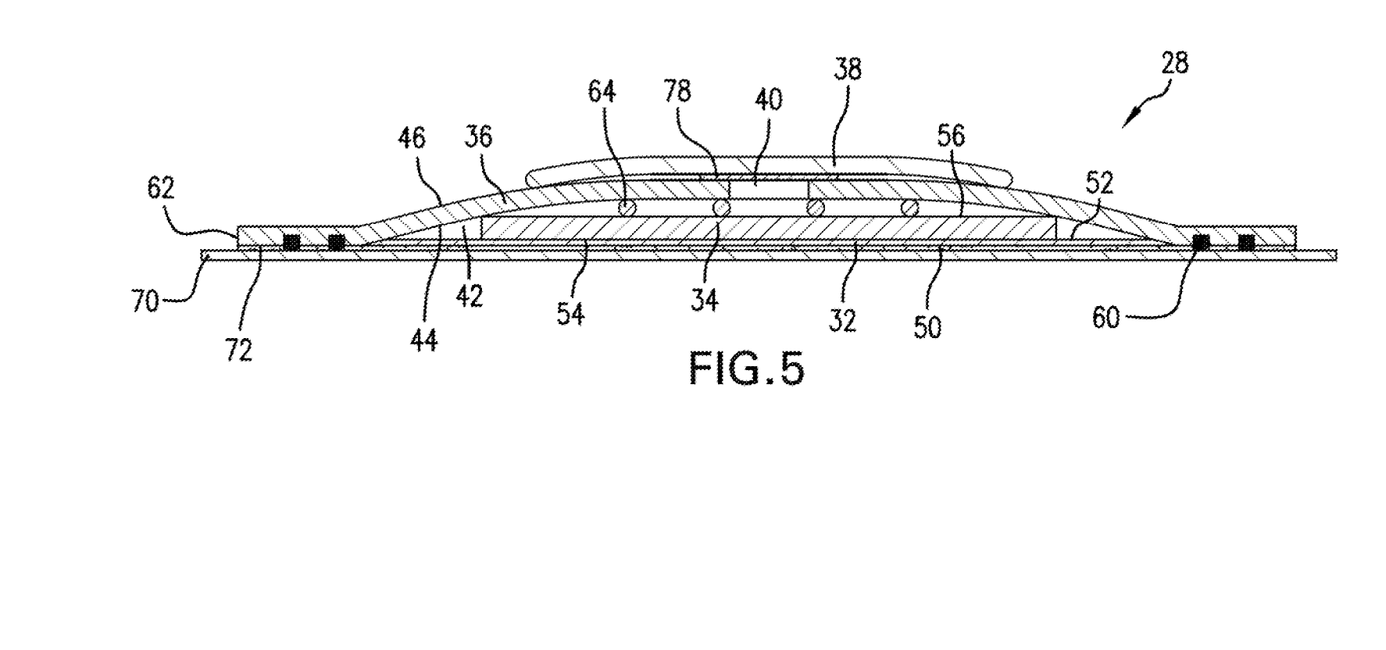
FIG. 5 is a cross-sectional view of another wound or tissue covering assembly.

The wound covering assembly 28 can also include an air permeable liquid impervious membrane 78 that covers the opening 40 in the drape 36. In the embodiment illustrated in FIGS. 3 and 4, the air permeable liquid impervious membrane 78 is affixed to the lower surface 44 of the drape 36; however, the air permeable liquid impervious membrane 78 could also be disposed on the outer surface 46 of the drape 36 covering the opening 40 in the drape 36, which is shown in FIG. 5. The air permeable liquid impervious membrane 78 precludes liquid (e.g., exudate) from traveling from the wicking element 34 through the opening 40 toward the pump assembly 30 when the pump assembly 30 is affixed to the wound covering assembly 28, such as that shown in FIG. 4. With reference to FIG. 5, when the air permeable liquid impervious membrane 78 is disposed on the outer surface 46 of the drape 36, the air permeable liquid impervious membrane 78 can be connected with the drape 36 using a resealable adhesive to allow for removal and later reattachment of the air permeable liquid impervious membrane 78 to the drape 36, which can allow for the addition or replacement of the wicking element 34. In the embodiment depicted in FIG. 5, the peel away layer 38 is connected with the drape 36 in a manner such that removal of the peel away layer 38 does not result in removal of the air permeable liquid impervious membrane 78. For example, in FIG. 5, the peel away layer 38 is larger than the air permeable liquid impervious membrane 78 and connection between the peel away layer 38 and the drape 36 (e.g., via adhesive, welding, or the like) is offset from a peripheral edge of the air permeable liquid impervious membrane 78 so that removal of the peel away layer 38 does not necessarily result in removal of the air permeable liquid impervious membrane 78.

Figure 6:
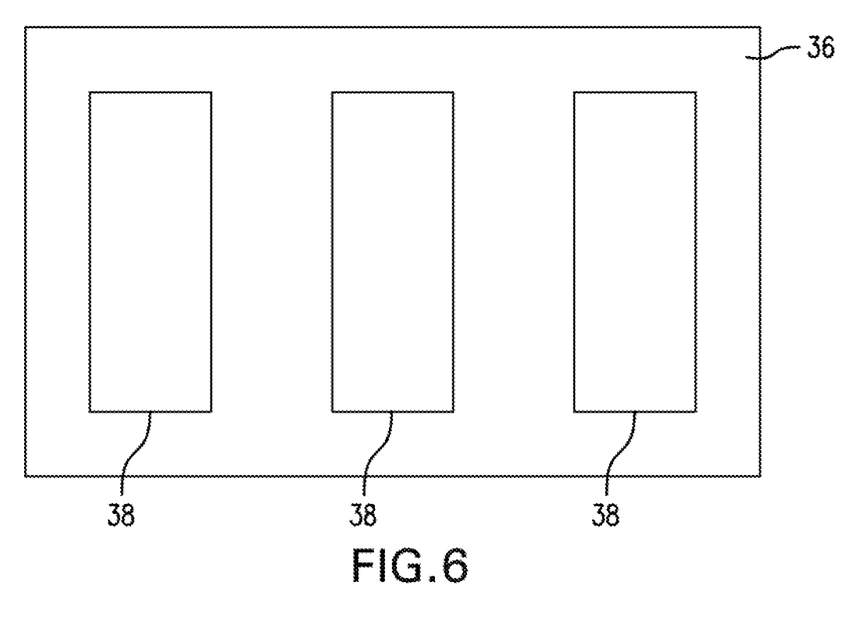
FIG. 6 is a top view of the covering assembly depicted in FIG. 5.

The peel away layer 38 covers the opening 40 (or openings if more than one is provided) in the drape 36. Only one peel away layer 38 is depicted in FIGS. 3-5, however, more than one peel away layer 38 can be provided. For example, FIG. 6 depicts a plurality of peel away layers 38 where each peel away layer 38 covers a respective opening 40 (not visible in FIG. 6) in the drape 36. The peel away layer 38 can be made from a thin, flexible film. Examples of such materials include polyurethane or polyethylene films. The peel away layer 38 is configured to inhibit passage of air and liquid through peel away layer 38 when the peel away layer 38 is covering the opening 40 in the drape 36. The peel away layer 38 can made from a material that is air and liquid impermeable, or the peel away layer 38 can be coated with a substance, e.g., a hydrogel or a hydrocolloid, or be metallized so as to be air and liquid impermeable.

As mentioned above, the peel away layer 38 is releasable from the drape 36 when the drape 36 is in contact with the skin 18 and covers the wound site 16. When the peel away layer 38 is removed from the drape 36, the opening 40 in the drape 36 is exposed to ambient. When the drape 36 is air and liquid impervious, removal of the peel away layer 38 can transform the wound covering assembly 28 from an occlusive dressing to a non-occlusive dressing. With the peel away layer 38 removed from the drape 36, the pump assembly 30 can be affixed to the wound covering assembly 28 or to the skin 18 to provide negative pressure to the wound site 16. With reference to FIG. 6, one of the peel away layers 38 can be removed and covered by a fitting connected with a mechanical pump (described in more detail below) and a second (or third, for example) peel away layer 38 can be removed exposing the respective opening 40 covered by the second (or third) peel away layer 38 to ambient. This can provide a non-occlusive breathable dressing connected to a mechanical pump, which can be useful with larger wounds that generate a relatively larger amount of exudate.

In the illustrated embodiment, the peel away layer 38 is shown as a separate layer from the drape 36 that is connected to the drape 36. The peel away layer 38 can be connected to the drape 36 via adhesive, welding or another similar connection around a periphery of the peel away layer 38 that would provide an air and liquid impermeable seal at the connection between the peel away layer 38 and the drape 36. Alternatively, the peel away layer 38 could be a removable section of the drape 36. Score lines can be cut into, but not through, the thickness of the drape 36 to define the peel away layer 38.

The pump assembly 30 generally includes a pump 100 and a pump drape 102. The pump drape 102 is configured to affix to the drape 36 or the skin 18 around the wound site 16 and cover the opening 40 in the drape 36 after the peel away layer 38 has been removed from the drape 36. FIG. 2 depicts the left side of the pump drape 102 affixed to the skin 18 and the right side affixed to the drape 36. The pump drape 102 could be made larger so that the pump drape 102 contacts the skin 18 and surrounds the peripheral edge 62 of the drape 36. Also, the pump drape 102 could be made smaller so that the pump drape 102 is affixed only to the drape 36.

The pump drape 102 includes a lower side 104 and an exterior side 106 opposite the lower side 104. The lower side 104 of the pump drape 102 is the side of the pump drape 102 that contacts the outer surface 46 of the drape 36 when the pump assembly 30 is affixed to the wound covering assembly 28 or that contacts the skin 18 when the pump drape 102 is affixed to the skin 18. The exterior side 106 of the pump drape 102 is exposed to ambient in the illustrated embodiment.

The pump assembly 30 also includes a pump sealing element, which can include a pump gasket 108 or adhesive 110. The pump sealing element 108, 110 can be positioned on the lower side 104 of the pump drape 102. The adhesive 110 can be an adhesive that is stronger or more aggressive than the adhesive 72 on the drape 36, for example when the adhesive 110 only comes in contact with the drape 36 and not the skin 18. The pump gasket 108 can be made from the same material, e.g. a hydrogel, and operate similarly to the sealing element 60. The pump gasket 108 can contact the human skin 18, for example when the pump drape 102 is larger than the wound covering assembly 28. The pump sealing element 108, 110 is configured preclude ingress of air between the pump drape 102 and the drape 36 when the pump drape 102 is affixed to the drape 36 or to preclude ingress of air between the pump drape 102 and the skin 18 when the pump drape 102 is affixed to the skin 18.

The pump assembly 30 also includes a pump drape release liner 112 that covers the pump sealing element, which can be the adhesive 110 or pump gasket 108. The pump drape release liner 112 is removed from the pump drape 102 prior to affixing the pump assembly 30 to the wound covering assembly 28 or the skin 18.

The pump 100 in the pump assembly 30 can be a reactor configured to react with a selected gas found in air, a zinc/air cell, a mechanical pump, or another small pumping device that can provide reduced pressure to the enclosed volume 42 through the opening 40 when the pump assembly 30 is affixed to the wound covering assembly 28. In an embodiment where the pump 100 is a reactor configured to react with a selected gas found in air, the reactor consumes the selected gas in the enclosed volume 42. In the embodiment where the pump 100 is such a reactor, the pump drape 102 covers the pump 100. An example of a reactor that can be used in the pump assembly 30 is described in US 2014/0109890A1. US 2014/0109890A1 describes an oxygen based heater; however, the oxygen based heater can be used as the reactor to consume oxygen within the enclosed volume 42 thus producing a partial vacuum within the enclosed volume 42. The reactor can include a reducing agent, a binding agent on a reactor substrate, and an electrolyte solution, which can be provided in an electrolyte impregnated pad. The reducing agent on the reactor substrate can be zinc, aluminum, or iron, for example.

The pump assembly 30 further includes an air permeable liquid impervious membrane 120, which can be similar to the air permeable liquid impervious membrane 78 that covers the opening 40 in the drape 36. In the embodiment where the pump 100 is a reactor that consumes oxygen in the enclosed volume 42, the reactor is interposed between the air permeable liquid impervious membrane 120 and the pump drape 102 when the pump drape 102 is affixed to the drape 36 covering the opening 40 in the drape 36. The air permeable liquid impervious membrane 120 can also envelope the pump 100.

With reference back to FIG. 3, the pump assembly 30 can also include a removable seal layer 130 that prevents the reactor from being exposed to ambient oxygen until after removal of the removable seal layer 130. In the embodiment where the pump 100 is the reactor configured to react with oxygen, both the pump drape release liner 112 and the removable seal layer 130 are removed from the pump assembly 30 prior to affixing the pump assembly 30 to the wound covering assembly 28 or to the skin 18. If desired, the pump drape release liner 112 can be attached to the removable seal layer 130 so that removal of the pump drape release liner 112 from the pump drape 102 results in removal of the removable seal layer 130 exposing the reactor to ambient. In another alternative arrangement, the pump drape release liner 112 can be affixed to the pump drape 102 in a manner to prevent the pump 100, which in this embodiment would be a reactor configured to consume oxygen, from being exposed to ambient until after removal of only the pump drape release liner 112, e.g., the removable seal layer 130 may not be provided.

Figure 7:
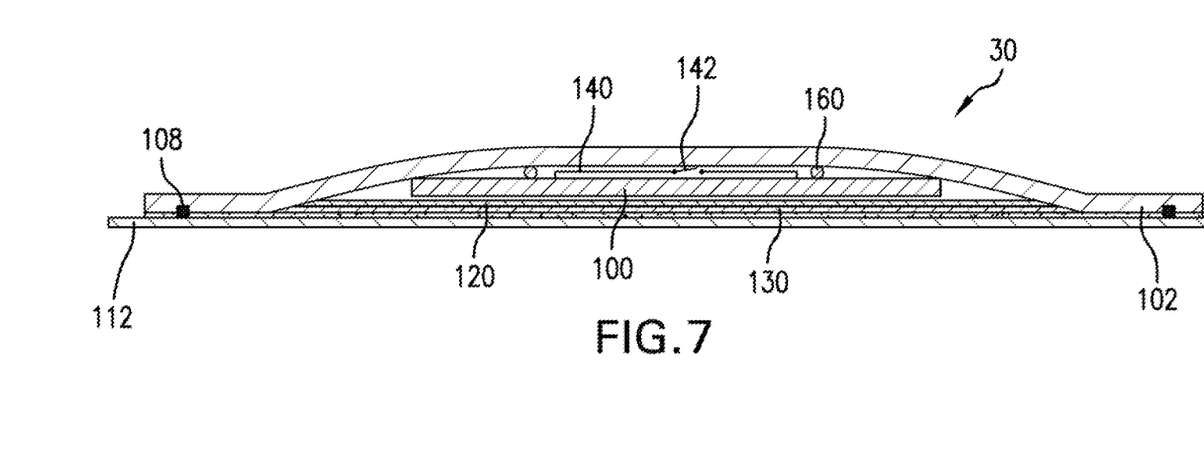
FIG. 7 is a cross-sectional view of an alternative pump assembly.

As mentioned above, the pump 100 could also be a zinc/air cell. When the pump 100 is a zinc/air cell, the zinc/air cell can react with oxygen found in the enclosed volume 42 (FIG. 3) to remove the oxygen within the enclosed volume 42 thus reducing pressure in the enclosed volume 42. In the embodiment where the pump 100 is a zinc/air cell, which is shown in FIG. 7, the pump drape 102 covers the pump 100. In the embodiment where the pump 100 is a zinc/air cell, a circuit 140 having a normally open switch 142 (both of which are depicted schematically in FIG. 7) can be connected to an anode and cathode, respectively, on the zinc/air cell. An operator can depress the pump drape 102, for example, in the vicinity of the switch 142 to close the switch 142. The zinc/air cell reacts with oxygen in the enclosed volume 42 (FIG. 3) to remove the oxygen from the enclosed volume 42 thus reducing the pressure within the enclosed volume 42. With continued reference to FIG. 7, the pump assembly 30 can also include the air permeable liquid impervious membrane 120 and the removable seal layer 130 that prevents the zinc/air cell from being exposed to ambient oxygen until after removal of the removable seal layer 130.

In lieu of the reactor and zinc/air cell described above, the pump 100 may be one or any combination of electrochemical pumps, vacuum-on-demand devices (referred to herein as VOD), electrolyzers, pressure-reducing solid state devices, oxygen absorbing iron packets, or getters of zirconium titanium, vanadium iron, lithium, lithium metal, magnesium, calcium, lithium barium combinations, zinc-air battery, zinc-air battery components or other materials highly reactive with the selected gases, for example, nitrogen, carbon dioxide and oxygen gases found in wound bed environments.

With reference back to FIG. 3, the pump assembly 30 can further include at least one spacer element 160 covered by the pump drape 102. The spacer element 160 in the pump assembly 30 can be similar in configuration and function to the spacer element 64 provided in the wound covering assembly 28. The spacer element 160 in the pump assembly 30 is configured to maintain spacing between the pump drape 102 and the drape 36 when reduced pressure is applied under the drape 36, i.e., within the enclosed volume 42.

The pump drape 102 covers the pump 100, which can be a reactor, and the spacer element 160 to define a chamber 162 that maintains at least a predefined chamber volume while the gas is being consumed from the enclosed volume 42. Since the drape 36 can made from a thin, flexible elastomeric film, as the gas is being consumed from the enclosed volume 42, the drape 36 can be drawn toward the wound site 16 and adjacent skin, which can reduce the volume of the enclosed volume 42. In accordance with the ideal gas law, if the volume of the enclosed volume 42 decreases, then the pressure in the enclosed volume 42 will increase from a relative negative pressure (with respect to ambient pressure) toward ambient pressure. Since it is desirable to maintain a relative negative pressure with respect to ambient pressure around the wound site 16, an increase in the pressure in the enclosed volume 42 toward ambient can be undesirable. By providing a chamber 162 having a predefined chamber volume, however, an overall system volume, which includes the enclosed volume 42 and the predefined chamber volume, can be provided even if the drape 36 draws toward the wound site 16 or the wicking element 34 begins to fill with exudate. Thus, relative negative pressure can be maintained in the overall system volume. This is because as the gas is being consumed from both the enclosed volume 42 and from the chamber 162, the predefined chamber volume is maintained even if the enclosed volume 42 is reduced.

The enclosed volume 42 is made up of a solid volume portion occupied by the wicking element 34 and an air volume portion occupied by air trapped in the enclosed volume 42. In the case of a therapeutic negative pressure system, utilized for wound care, the range of reported operating pressures, relative to standard atmospheric pressure of 760 mmHg, are from −60 mmHg to −200 mmHg (absolute pressures of 560 to 700 mmHg). Where the pump 100 is a reactor configured to consume oxygen, after all of the molecules of oxygen have been consumed by the reactor from the air in the overall system volume, the gas pressure in the overall system volume is reduced by 21% (or 159.6 mmHg) assuming that the overall system volume was to remain constant. Thus, with the ideal case delivering maximum potential of −159.6 mmHg with dry air (note that the presence of humidity can change this number), designing a system to deliver the correct operating pressure, accounting for changes in the volume of the enclosed volume 42 and exudate entering the wicking element 34 and displacing air, is a formidable task.

The negative pressure device 26 accomplishes this task by dividing the negative pressure system into two parts: the wound covering assembly 28 (or bandage part) and the pump assembly 30. The wound covering assembly 28 (bandage part) functions as a bandage so as to be flexible and absorb fluid (exudate) as necessary. Additionally, the wound covering assembly 28, while connected to the pump assembly 30, functions to hinder the movement of fluid between the two assemblies while remaining in pneumatic communication. By absorbing fluid (exudate) only in the wound covering assembly 28, one can minimize the effect of volume loss, and thus pressure loss, on the system. The materials that make up the wound covering assembly 28 can be soft and compliant, and the pump assembly 30 includes more rigid components to reduce volume loss in the pump assembly 30 so as to increase the likelihood that the pressure in the overall volume of the system stays in the therapeutic range. In view of the aforementioned, it is desirable to have the predefined chamber volume to be at least six times as large as the initial air volume portion (prior to the reactor consuming oxygen in this example) of the enclosed volume 42.

Figure 8:
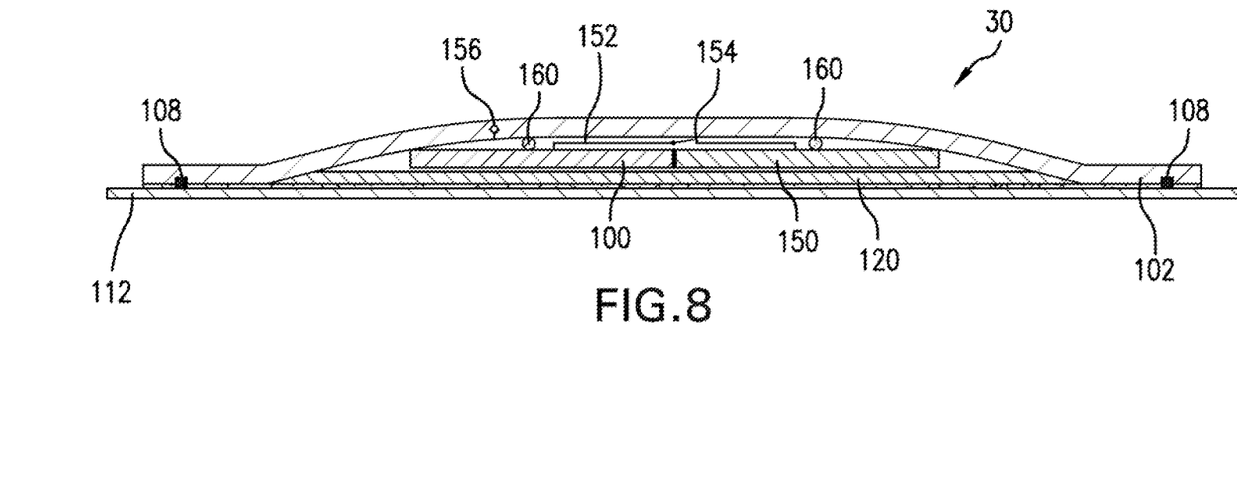
FIG. 8 is a cross-sectional view of another alternative pump assembly.

As discussed above, the pump 100 can also be a mechanical pump. One such embodiment is schematically depicted in FIG. 8. In the embodiment depicted in FIG. 8, the pump assembly 30 can further include a power source 150, which is electrically connected with the pump 100, and is also connected with the pump drape 102. In the embodiment where the pump 100 is a mechanical pump, a circuit 152 can be provided with a normally open switch 154. An operator can depress the pump drape 102, for example, to close the switch 154 to provide power from the power source 150, which can be a small battery, to the pump 100. In the embodiment where the pump 100 is a mechanical pump, a one-way check valve 156 can be provided in the pump drape 102 to allow for gas to move from the enclosed volume 42 through the one-way check valve 156 into ambient; however, ambient air is precluded from passing through the check valve 156 toward the enclosed volume 42.

The pump assembly 30 can also include an opening (similar to the opening 40) in the pump drape 102 covered by a pump peel away layer (similar to the peel away layer 38). Removal of the pump peel away layer can expose the opening in the pump drape 102 to allow for replacement of the pump 100. The pump peel away layer would connect with the pump drape 102 in the same way that the peel away layer 38 connects with the drape 36. The pump peel away layer would be made from the same material as the peel away layer 38.

Figure 9:
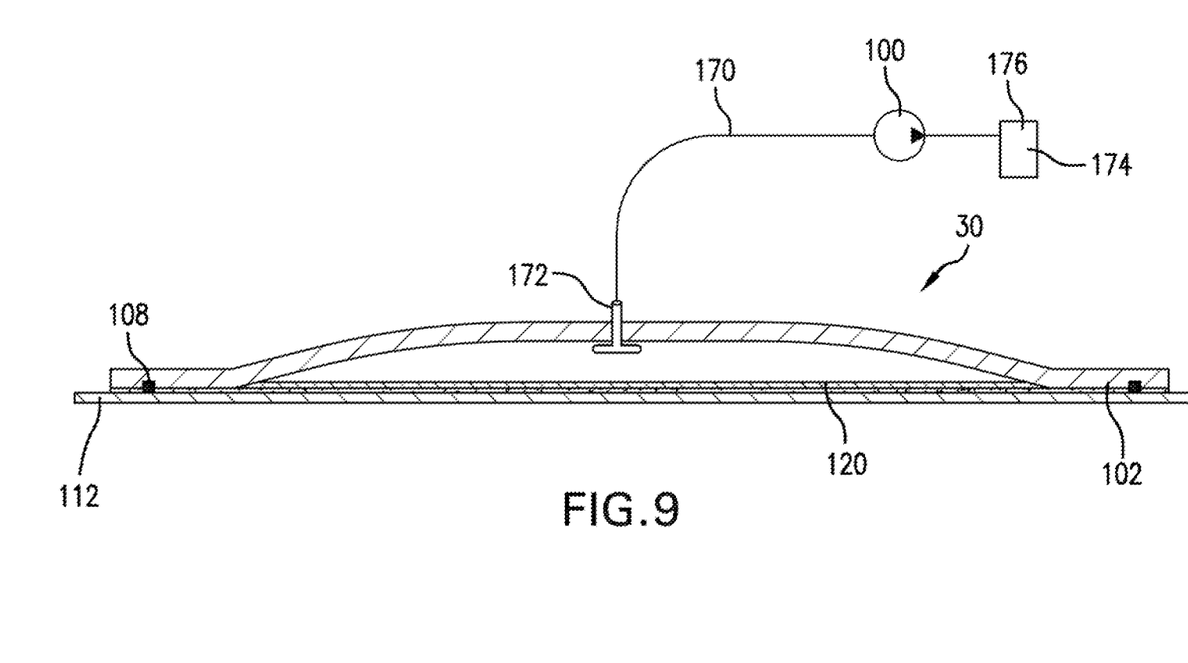
FIG. 9 is a cross-sectional view of another alternative pump assembly.

Another embodiment of a mechanical pump is shown in FIG. 9. In this embodiment, the pump 100 is connected with the pump drape 102 through a fluid line 170 and the pump 100 is located externally from the pump drape 102. A fitting 172 passes through the pump drape 102, and the fluid line 170 connects the fitting 172, which includes an internal passage, with the pump 100. The pump 100 connects with a canister 174 through an exhaust line 176.

Figure 10:
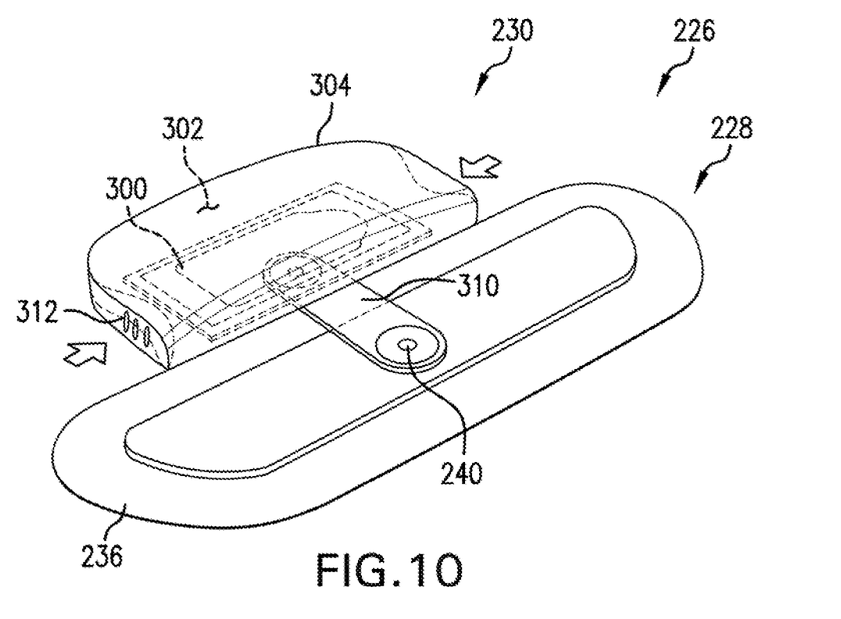
FIG. 10 is a schematic depiction of an alternative negative pressure device including a wound or tissue covering assembly and another alternative pump assembly.

FIG. 10 depicts another embodiment of a negative pressure device 226 including a wound covering assembly 228 and a pump assembly 230. The wound covering assembly 228 can be similar to the wound covering assembly 28 described above and include a drape 236 including an opening 240. The drape 236 is made from a flexible material that inhibits passage of liquid and air through the drape 236 other than through the opening 240. The drape 236 covers a wicking element (not visible), which is similar to the above-described wicking element 34. The wound covering assembly 228 is also provided with a sealing element (not visible), which is similar in construction and function to the sealing element 60 described above. The sealing element surrounds the wicking element and when applied to skin cooperates with the drape 236 to define an enclosed volume (similar to the above-described enclosed volume 42) covered by the drape 236 and surrounded by the sealing element. Air within the enclosed volume is inhibited from exiting the enclosed volume other than through the opening 240.

The pump assembly 230 includes a pump 300, which is a reactor configured to react with a gas found in air to consume the gas in the illustrated embodiment. The reactor is positioned within a chamber 302 that is in fluid communication with the enclosed volume defined by the wound covering assembly 228 via the opening 240. In the embodiment depicted in FIG. 10, it is a rigid container 304 that is in fluid communication with the enclosed volume and defines the chamber 302. The chamber 302, like the chamber 162 described above, is configured to maintain a predefined chamber volume while the gas being consumed by the reactor is being consumed from the enclosed volume. Accordingly, if the enclosed volume decreases in volume as the gas in the enclosed volume is being consumed, the predefined chamber volume is maintained.

In FIG. 10, a connector 310 mechanically connects the rigid container 304 with the wound covering assembly 228 and pneumatically connects the chamber 302 with the enclosed volume. An air permeable liquid impervious element (not visible in FIG. 10 but similar to the air permeable liquid impervious membrane 120 described above) is interposed between the chamber 302 and the enclosed volume and is configured to preclude liquid (exudate) drawn into the enclosed volume from entering the chamber 302. As such, by absorbing fluid (exudate) only in the wound covering assembly 228, one can minimize the effect of volume loss, and thus pressure loss, on the overall system.

The rigid container 304 in FIG. 10 can include finger recesses 312 at which the rigid container 304 can be squeezed or depressed to activate the reactor such that after activation the reactor begins to consume a selected gas from air within the chamber 302 and the enclosed volume. For example, by squeezing the rigid container 304 at the finger recesses 312, a seal layer that prevents the reactor from being exposed to ambient can be pierced thus exposing the reactor to air. Other manners in which the reactor can be activated will be described in more detail.

Figure 11:
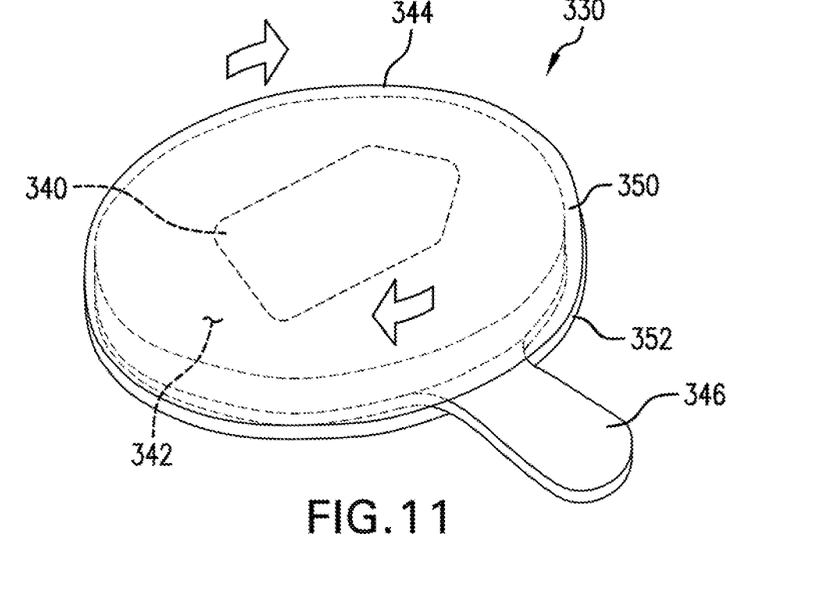
FIG. 11 is a schematic depiction of another alternative pump assembly for use with the covering assembly depicted in FIG. 10.

FIG. 11 depicts a pump assembly 330 that includes a pump 340, which is a reactor configured to react with a gas found in air to consume the gas. The reactor is positioned within a chamber 342 defined by a rigid container 344. A connector 346, which is similar to the connector 310, can mechanically connect the rigid container 344 with a wound covering assembly, such as the wound covering assembly 228 in FIG. 10, and pneumatically connect the chamber 342 with the enclosed volume defined by the wound covering assembly. The chamber 342, like the chamber 162 described above, is configured to maintain a predefined chamber volume while the gas being consumed by the reactor is being consumed from the enclosed volume defined by the wound covering assembly to which the pump assembly 330 is connected. The rigid container 344 can include a lid 350 that fits onto a base 352. The reactor can be activated by rotating the lid 350 with respect to the base 352.

Figure 12:
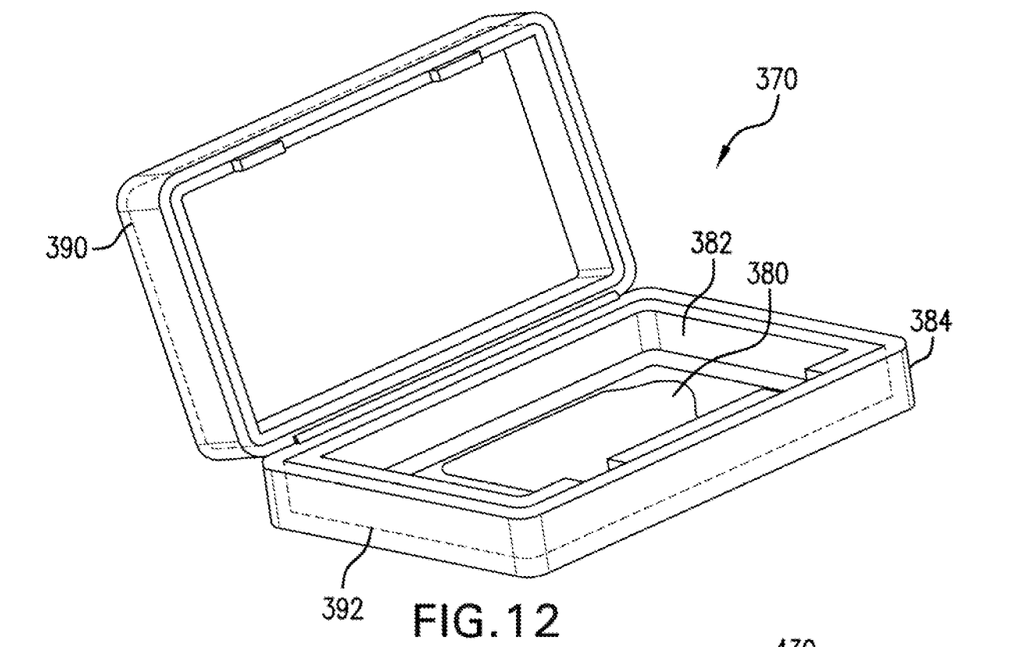
FIG. 12 is a schematic depiction of another alternative pump assembly for use with the covering assembly depicted in FIG. 10.

FIG. 12 depicts a pump assembly 370 that includes a pump 380, which is a reactor configured to react with a gas found in air to consume the gas. The reactor is positioned within a chamber 382 defined by a rigid container 384. A connector similar to the connector 310 can mechanically connect the rigid container 384 with a wound covering assembly, such as the wound covering assembly 228 in FIG. 10, and pneumatically connect the chamber 382 with the enclosed volume defined by the wound covering assembly. The chamber 382, like the chamber 162 described above, is configured to maintain a predefined chamber volume while the gas being consumed by the reactor is being consumed from the enclosed volume defined by the wound covering assembly to which the pump assembly 370 is connected. The rigid container 384 can include a lid 390 pivotally connected with a base 392. To activate the reactor, the lid 390 is pivoted with respect to the base 392 to expose the reactor. If the reactor is covered by a removable seal layer that prevents the reactor from being exposed to ambient until after removal of the removable seal layer, then the removable seal layer can be removed when the lid 390 is pivoted away from the base 392. After activation of the reactor, the lid 390 closes and seals against the base 392 to define the chamber 382.

Figure 13:
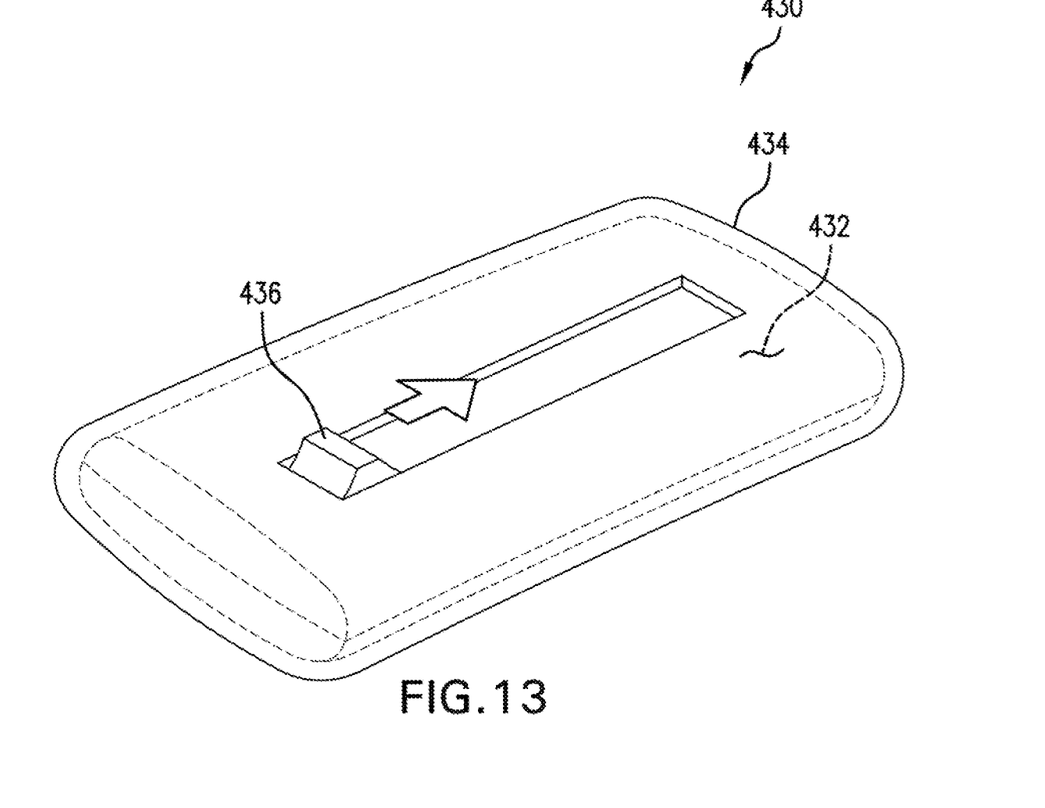
FIG. 13 is a schematic depiction of another alternative pump assembly for use with the covering assembly depicted in FIG. 10.

FIG. 13 depicts a pump assembly 430 that includes a pump (not visible), which is a reactor configured to react with a gas found in air to consume the gas. The reactor is positioned within a chamber 432 defined by a rigid container 434. A connector similar to the connector 310 can mechanically connect the rigid container 434 with a wound covering assembly, such as the wound covering assembly 228 in FIG. 10, and pneumatically connect the chamber 432 with the enclosed volume defined by the wound covering assembly. The chamber 432, like the chamber 162 described above, is configured to maintain a predefined chamber volume while the gas being consumed by the reactor is being consumed from the enclosed volume defined by the wound covering assembly to which the pump assembly 430 is connected. An actuator 436 can move with respect to the rigid container 434 to activate the reactor. For example, to activate the reactor, the actuator 436 slides with respect to the rigid container 434. The actuator 436 can connect with a cutting element to cut through a seal layer that prevents the reactor from being exposed to ambient until after seal layer has been pierced.

A method of treating the wound site 16 will be described with reference to the wound covering assembly 28 depicted in FIG. 3 and the pump assemblies 30 depicted in FIGS. 3, 4 and 7-9. Nevertheless, the method of treating the wound site 16 can be accomplished using a wound covering assembly that is structurally different than the wound covering assembly 28 depicted in FIG. 3 or a pump assembly that is structurally different than the depicted pump assemblies 30.

The method of treating the wound site 16 includes placing the lower surface 44 of the drape 36 of the wound covering assembly 28 on the skin 18 surrounding the wound site 16. The drape 36 includes the opening 40. The method can further include removing the peel away layer 38 from the drape 36 to expose the opening 40 to ambient. The method also includes affixing the pump assembly 30 to the drape 36 or the skin 18 to cover the opening 40 in the drape 36. Where the pump assembly includes a reactor or zinc/air cell configured to react with a selected gas found in air and the removable seal layer 130 that prevents the reactor or zinc/air cell from being exposed to ambient until after removal of the removable seal layer, the method can further include removing the removable seal layer 130 and exposing the pump 100 to ambient prior to affixing the pump assembly 30 to the drape 36 or the skin 18. Where the pump assembly includes a zinc/air cell as the pump 100, the method can include closing the electrical circuit 140 (FIG. 7), which includes the zinc/air cell. Also, in the embodiment where the pump assembly includes a mechanical pump as the pump 100, the method can also include closing the electrical circuit 152, which includes the mechanical pump and the power source 150.

Controlling the volume around the wound site 16 can be important to maintain negative pressure. Both the drape 36 and the pump drape 102 can be made from thin films that may collapse toward the wound site 16 as gas is being removed from around the wound site. The spacer elements 64, 160 can maintain adequate spacing between the drapes 36, 102 and the wound site 16 or skin 18 when reduced pressure is applied under the drapes 36, 102.

Also, in some instances the peel away layer 38 may not be provided. In instances where the peel away layer 38 is not provided, the negative pressure device 26 can still have a two-piece design, e.g., include the wound covering assembly 28 and the pump assembly 30. In instances where the peel away layer 38 is not provided, the drape 36 can include the opening 40 (or multiple openings) that are covered by the pump drape 102 and the remainder of the pump assembly 30. In instances where the peel away layer 38 is not provided, the drape 36 can also be made from a material that allows gas to permeate through the drape 36.

Alternatively, the negative pressure device 26 can have a one-piece design without the peel away layer 38. In such an instance, the wound contacting element, which can include the wound contact layer 32 or the wicking element 34, a drape (e.g., an outer drape similar to the pump drape 102), the pump 100 and the spacer element (e.g., similar to the spacer element 64, 160) can be provided as one assembly that is affixed to the skin 18 as one unit. In this instance, an inner drape (similar to the drape 36 in FIG. 4) may not be provided. In this alternative arrangement, the drape is configured to inhibit passage of air and liquid through the drape. In this alternative arrangement, a sealing element, which is similar to the sealing element 60 described above, can be positioned on a skin contacting side of the wound contacting element or on a lower surface of the drape. In this alternative arrangement, the pump is covered by the drape and can be any of the pumps described above. In this alternative arrangement, the negative pressure device 26 can include an air permeable liquid impervious membrane, similar to the air permeable liquid impervious membrane 120. Where the pump is a reactor, described above, the pump is interposed between the air permeable liquid impervious membrane and the drape when the drape is affixed to skin 18 covering the wound site 16. In this alternative arrangement where the pump is a reactor, the negative pressure device can also include a removable seal layer that prevents the reactor from being exposed to ambient until after removal of the removable seal layer. In this alternative arrangement, the negative pressure device 26 can also include a release liner disposed over a lower surface of the drape, and the release liner is removable to expose an adhesive provided on a lower surface of the drape.

Embodiments of a negative pressure device and methods of treating a wound site have been described above in particularity. Modifications and alterations will occur to those upon reading and understanding the preceding detailed description. The invention, however, is not limited to only the embodiments described above. Instead, the invention is broadly defined by the appended claims and the equivalents thereof. It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A negative pressure device comprising:
a wound covering assembly including
a drape including an opening and being made from a flexible material that inhibits passage of liquid and air through the drape other than through the opening,
a wicking element covered by the drape, and
a sealing element surrounding the wicking element and when applied to skin cooperating with the drape to define an enclosed volume covered by the drape and surrounded by the sealing element such that air within the enclosed volume is inhibited from exiting the enclosed volume other than through the opening, and
a reactor configured to react with a gas found in air to consume the gas;
a seal layer covering the reactor that prevents the reactor from being exposed to ambient until after the seal layer has been removed, pierced or cut;
a container defining a chamber, the reactor being positioned in the chamber and the chamber being configured to maintain a predefined chamber volume while the gas is being consumed from the enclosed volume; and
a connector mechanically connecting the container with the wound covering assembly, the chamber being in fluid communication with the enclosed volume via the connector.

2. The negative pressure device of claim 1, wherein the container is offset from the drape.

3. The negative pressure device of claim 1, wherein the container is configured to pierce the seal layer that prevents the reactor from being exposed to ambient.

4. The negative pressure device of claim 3, wherein the container is configured to be squeezed to pierce the seal layer.

5. The negative pressure device of claim 1, wherein the container includes a lid and a base, wherein the reactor is activated by rotating the lid with respect to the base.

6. The negative pressure device of claim 1, wherein the container includes a lid and a base, wherein the lid is pivoted with respect to the base to expose the reactor.

7. The negative pressure device of claim 1, further comprising an actuator, wherein the actuator moves with respect to the container to activate the reactor.

8. The negative pressure device of claim 7, wherein the actuator slides with respect to the container to activate the reactor.

9. The negative pressure device of claim 7, wherein the actuator moves with respect to the container to cut through the seal layer.

10. The negative pressure device of claim 1, wherein the container is a rigid container.

11. The negative pressure device of claim 1, wherein the enclosed volume includes a solid volume portion occupied by the wicking element and an initial air volume portion occupied by air trapped in the enclosed volume prior to the reactor consuming the gas, wherein the predefined chamber volume is at least six times larger than the initial air volume portion.

12. The negative pressure device of claim 1, further comprising a removable layer or portion covering the opening, the removable layer or portion being configured to inhibit passage of air and liquid through the removable layer or portion and the drape other than through the opening after the removable layer or portion has been removed to expose the opening to ambient.

13. The negative pressure device of claim 1, wherein the reactor is configured to consume oxygen.

14. A method of treating a tissue site, the method comprising:
affixing a drape to skin surrounding a tissue site and covering a wicking element, the drape including an opening and being made from a flexible material that inhibits passage of liquid and air through the drape other than through the opening;
sealing around the tissue site with a sealing element cooperating with the drape to define an enclosed volume covered by the drape and surrounded by the sealing element;
connecting a container defining a chamber to the drape with a connector such that the chamber is in fluid communication with the enclosed volume via the connector, wherein a reactor configured to react with a gas found in air to consume the gas is disposed in the chamber, and the chamber is configured to maintain a predefined chamber volume while the reactor consumes the gas in the enclosed volume;
actuating the container or an actuator on the container to activate the reactor by removing, cutting or piercing a seal layer that prevents the reactor from being exposed to ambient until after the seal layer has been removed, cut or pierced.

15. The method of claim 14, wherein connecting the container further includes connecting the container so that the container is offset from the drape.

* * * * *